US008784805B2

(12) United States Patent
Brands

(10) Patent No.: US 8,784,805 B2
(45) Date of Patent: Jul. 22, 2014

(54) METHOD FOR INCREASING THE ACTIVITY OF THE IMMUNE SYSTEM OF A MAMMAL AT RISK OF INFLAMMATORY DISEASES

(75) Inventor: Rudi Brands, Bunnik (NL)

(73) Assignee: Alloksys Life Sciences B.V., Bunnik (NL)

( * ) Notice: Subject to any disclaimer, the term of this patent is extended or adjusted under 35 U.S.C. 154(b) by 556 days.

(21) Appl. No.: 12/919,091

(22) PCT Filed: Feb. 27, 2009

(86) PCT No.: PCT/EP2009/001603
§ 371 (c)(1),
(2), (4) Date: Nov. 22, 2010

(87) PCT Pub. No.: WO2009/106368
PCT Pub. Date: Sep. 3, 2009

(65) Prior Publication Data
US 2011/0052560 A1  Mar. 3, 2011

(30) Foreign Application Priority Data

Feb. 29, 2008  (WO) ................ PCT/EP2008/001767

(51) Int. Cl.
A61K 38/46  (2006.01)
(52) U.S. Cl.
USPC ................ 424/94.6; 424/94.1; 424/94.61
(58) Field of Classification Search
None
See application file for complete search history.

(56) References Cited

U.S. PATENT DOCUMENTS 5,852,024 A * 12/1998 Pines et al. ............... 514/266.22
2006/0182733 A1   8/2006 Bach et al.

FOREIGN PATENT DOCUMENTS

| EP | 0721501 B1 | 6/2005 |
| WO | 02071062 A2 | 9/2002 |
| WO | 2004084933 A1 | 10/2004 |
| WO | 2005074978 A1 | 8/2005 |
| WO | 2007055760 A2 | 5/2007 |
| WO | 2007109582 A2 | 9/2007 |

OTHER PUBLICATIONS

Lydyard, P.M. et al. BIOS Instant Notes in Immunology, Second Edition [online], New York, NY: Garland Science/BIOS Scientific Publishers Ltd., 2004 [retrieved on Apr. 8, 2013]. Retrieved from the Internet<URL: http://www.tandfebooks.com/doi/pdf/10.4324/9780203488287>.*
Hubbard, WJ et al. Cecal ligation and puncture. Shock. 2005. 24(Suppl. 1): 52-57.*
Laroche, M. and Harding, G. Primary and secondary peritonitis: an update. Eur. J. Clin. Microbiol. Infect. Dis. 1998. 17: 542-550.*
Poelstra et al., "A Single Injection of Alkaline Phosphatase Significantly Attenuates The Inflammatory Response Upon Lipopolysaccharide (LPS) In Serum and in Livers of Mice", Hepatology, 2001, vol. 34(4), p. A279.
Zernecke et al., "CD73/Ecto-5'-Nucleotidase Protects Against Vascular Inflammation and Neointima Formation", Circulation, May 2, 2006, vol. 113, pp. 2120-2127.
Van Veen et al., "Bovine Intenstinal Alkaline Phosphatase Attenuates the Inflammatory Response in Secondary Peritonitis in Mice", Infection and Immunity, Jul. 2005, vol. 73(7), pp. 4309-4314.
Quigley, "The Therapeutic Potential of CD39: Interview With Dr. Simon Robson", Expert Opin. Ther. Targets, 2006, vol. 10(5), pp. 649-652.
Robson et al., "Ectonucleotidases of CD39 Family Modulate Vascular Inflammation and Thrombosis in Transplantation", Seminars in Thrombosis and Hemostasis, 2005, vol. 31(2), pp. 217-233.
Poelstra et al. Dephosphorylation of Endotoxin by Alkaline Phosphatase in Vivo. Am J Pathology; 1997; pp. 1163-1169; vol. 151; No. 4.
Tuin et al. On the Role and Fate of LPS-dephosphorylating Activity in the Rat Liver. Am J Physiol Gastrointest Liver Physiol.; 2006; pp. G377-G385; vol. 290.
Van Veen et al. Alkaline Phosphatase Reduces Hepatic and Pulmonary Injury in Liver Ischemia-Reperfusion Combined with Partial Resection. British J Surgery; 2006; pp. 448-456; vol. 93.
Verweij et al. Protection Against an *Escherichia coli*-induced Sepsis by Alkaline Phosphatase in Mice. Shock; 2004; pp. 174-179; vol. 22; No. 2.
Bentala et al. Removal of Phosphate from Lipid A as a Strategy to Detoxify Lipopolysaccharide. Shock; 2002; pp. 561-566; vol. 18; No. 6.

* cited by examiner

Primary Examiner — Allison Ford
Assistant Examiner — Susan E Fernandez
(74) Attorney, Agent, or Firm — The Webb Law Firm

(57) ABSTRACT

The present invention relates to methods for increasing the activity of the immune system and, especially, to methods for increasing the activity of the immune system by modulation of endogenous ectophosphatase levels. According to a particularly preferred embodiment the present invention relates to methods for the prophylaxis of mammals, and especially human mammals, at risk of inflammatory diseases such as mammals suffering from conditions such as surgery, digestive tract diseases, respiratory diseases, skin diseases, burn wounds, smoke inhalation, intoxication, severe blood loss, food poisoning, chemotherapy, radiation therapy, severe trauma or liver diseases, immunocompromised conditions. For this, the present invention provides use of an ectophosphatase for the preparation of a medicament for the prophylaxis of a mammal at risk of inflammatory diseases.

8 Claims, 3 Drawing Sheets

METHOD FOR INCREASING THE ACTIVITY OF THE IMMUNE SYSTEM OF A MAMMAL AT RISK OF INFLAMMATORY DISEASES

FIELD OF THE INVENTION

The present invention relates to methods for increasing the activity of the immune system and, especially, to methods for increasing the activity of the immune system by modulation of endogenous ectophosphatase levels. According to a particularly preferred embodiment, the present invention relates to methods for the prophylaxis of mammals, and especially human mammals, suffering from—or at risk of—inflammatory conditions and diseases such as mammals suffering from conditions such as surgery, digestive tract diseases, respiratory diseases, skin diseases, burn wounds, smoke inhalation, intoxication, severe blood loss, food poisoning, chemotherapy, radiation therapy, severe trauma or liver diseases.

BACKGROUND OF THE INVENTION

Phosphatases are a group of enzymes capable of dephosphorylating or phosphorylate a substrate, i.e., the enzyme hydrolyzes phosphoric acid monoesters into a phosphate ion and a molecule with a free hydroxyl group or vice versa.

Ectophosphatases are a subclass of phosphatases which function extracelluarly, i.e., are capable of dephosphorylating an extra-cellular substrate in the extra-cellular space. This in contrast with intracellular phosphatases (also designated as kinases) (de)phosphorylating an intra-cellular substrate inside the cell, i.e., the intracellular space. The intra-cellular phosphatases are often involved in signal transduction.

Ectophosphatases can be in the form of integral membrane or GPI-anchored proteins displaying their catalytic domain, i.e., the domain involved in the actual dephosphorylating of a substrate, to the extra-cellular space. As an alternative, ectophosphatases can be present in the extra-cellular space as secreted or soluble proteins.

Ectophosphatases, and especially alkaline phosphatases (also designated in the art as AP, ALP or APhos), have been reported to be implicated in attenuation of inflammatory insults through their phosphatase activity on substrates such as, amongst others, endotoxins and nucleotides. Other ectophosphatases, like CD39 and CD73 (nucleotidases, apyrases), have been implicated in prevention of thrombolysis.

Alkaline phosphatase (ALP) (EC 3.1.3.1) is a hydrolase enzyme responsible for removing phosphate groups from many types of molecules, including nucleotides, proteins, and alkaloids. As is indicated by the name, alkaline phosphatases are most effective in an alkaline environment.

In humans, ectophosphatases, like alkaline phosphatase, are present in all tissues throughout the entire body, but are particularly concentrated in liver, bile duct, kidney, bone, and placenta.

Known species of alkaline phosphates are, for example, Bacterial alkaline phosphatase (BAP), Shrimp alkaline phosphatase (SAP), Calf intestine alkaline phosphatase (CIAP), Bovine intestinal alkaline phosphates (bIAP), and Placental alkaline phosphatase (PLAP) and its C terminally truncated version that lacks the last 24 amino acids (constituting the transmembrane domain)—the secreted alkaline phosphatase (SEAP).

Human alkaline phosphatises are catagorised as tissue nonspecific alkaline phosphatises (also referred as TNSAP or bone/liver/kidney type) and tissue specific alkaline phosphatises (placental/intestinal and germ cell type). To the TNSAP's also belongs, for example, alkaline phosphate present in milk and expressed by white blood cells.

Ecto-nucleoside Triphosphate Diphosphohydrolase 1, also designated in the art as CD39 or apyrase, is a nucleotide metabolizing enzyme belonging to a family of acid anhydride hydrolases. Examples of other enzymes belonging to this family are GTP phosphohydrolase, pyrophosphatase and thiamin-triphosphatase.

The ectophosphatase was first identified in 1949 and in 1963 partially purified from potato. The enzyme is also known under its registry number EC 3.6.1.5.

Apyrases are naturally occurring transmembrane glycoproteins that can activate intracellular pathways upon activation. Apyrases are found in a large number of microbial species such as *E. coli, Aspergillus fumigatus* and *Kluyveromyces lactis*, plants such as *Arabidopsis thaliana, Glycine max* and *Oryza sativa*, insects such as *Drosophila melanogaster* and mammals like *Rattus norvegicus, Mus musculus* and *Homo sapiens*.

An apyrase enzyme comprises three domains, an extracelluar, a transmembrane and an intracellular domain. The extracellular domain comprises a conserved catalytic region responsible for the catalytic activity of the extracellular enzyme.

The catalytical domain catalyzes the hydrolysis of ATP to yield AMP and orthophosphate. Such activity can thus be characterized as an ATP-diphosphatase or ATP diphosphohydrolase. It can also act on ADP, again yielding AMP and orthophosphate. This activity can be characterized as an ADPase or ADP phosphohydrolase. Based on the combined enzymatic activities of the catalytic domain, the enzyme can also be regarded as an ATP-ADPase.

Reported physiological functions of apyrases address their possible involvement in maintenance of haemostasis and inhibition of platelet aggregation through hydrolysis of extracellular ADP, which is released from activated thrombocytes upon vascular injury.

CD73, also an ectophosphatase, converts monophosphate nucleotides like AMP to nucleosine+phosphate. (Nucleosine is non-inflammatory, whereas ATP and ADP and to lesser degree AMP are pro-inflammatory moieties, once presented extracellularly.

SUMMARY OF THE INVENTION

The present invention is based on the surprising discovery that, besides the above reported activities of ectophosphatases, this group of phosphate enzymes are also capable of modulating the activity on the immune system, i.e., they are capable increasing, maintaining, boosting, or preventing deterioration of a compromised immune system.

Such compromised immune system can, for example, be the result of surgery, digestive tract diseases, respiratory diseases, skin diseases, burn wounds, smoke inhalation, intoxication, severe blood loss, food poisoning, chemotherapy, radiation therapy, severe trauma and liver diseases.

Accordingly, the present invention relates to the use of an ectophosphatase for the preparation of a medicament for the prophylaxis of a mammal, preferably a human mammal, at risk of or suffering from inflammatory diseases and conditions.

The term "prophylaxis", as used herein, is used to indicate a measure taken for the prevention of a disease or condition, in the present case preventing progression or initiation of an inflammatory disease.

Accordingly, the present use of ectophosphatases relates to administering the present medicament to mammal, and especially a human mammal, suffering from or at risk of an inflammatory disease, thereby preventing, or attenuating, an inflammatory condition or the treatment thereof when opportunistic.

It was previously described that using supplemental ectophosphatases as prophylactic treatment results in reduced pro-inflammatory cytokine levels in several inflammation animal models. The present invention demonstrates that supplemental alkaline phosphatase in patients undergoing surgery not only such anti-inflammatory responses are observed, but also an induction is evoked of an endogenous secondary alkaline phosphatase that is inhibited by L-HA (L-homo arginin), known to act as an inhibitor of tissue non specific AP.

A bolus of AP (bIAP), followed by a 36 hours intravenous infusion (5.6 IU/kg/hour) was intravenously administered to patients resulting in a peak plasma level of AP immediately after administration with a kinetic profile compatible with the administered AP.

Surprisingly however, the endogenous AP that emerges is an AP with the kinetic profile having an observed overall plasma residence time in the order of about 20-22 hours. This induced type phosphatase was sensitive for 1-homoarginin and consequently is most likely Tissue Non Specific AP (e.g. liver type). Another candidate TNSAP alkaline phosphatase enzyme (bone type) was shown not to be induced.

Hence, where administration of AP during acute inflammation is reported to combat local or systemic endotoxin- and other phosphate-containing substrates-induced inflammation, AP prophylaxis improves the defense against a new inflammatory insult by triggering the release of sustainable alkaline phosphates in the circulation.

The surprising implication of this provides, amongst others, the following advantages:
- AP acts like an acute phase protein, where high levels of physiological active AP have a protective anti-inflammatory effect;
- Supplemental pre-surgical plasma levels benefit clinical outcome in acute inflammation;
- Patients suffering from or at risk of inflammatory conditions/diseases are protected by pre-treatment or treatment with physiological active AP, which will elevate their endogenous physiological levels
- retreatment of AP supplementation during surgery or at time points post surgery will perpetuate the induction the endogenous alkaline phosphatase. The anti inflammatory effects of alkaline phosphatase thus are prolonged.

According to a preferred embodiment of the present invention, the ectophosphatase is selected from the group consisting of alkaline phosphatase, nucleotidase and apyrase.

According to another preferred embodiment of the present invention, the prophylaxis is provided by an induction of endogenous ectophosphatase levels, i.e., an increase in ectophosphatase levels produced by the mammal itself and not provided by an heterologous source such as, for example, administering additional supplemental alkaline phosphatase.

According to yet another preferred embodiment of the present invention, the risk of inflammatory disease comprises conditions resulting in a decreased activity of the immune system. Such risk is preferably selected from the group consisting of surgery, digestive tract diseases, respiratory diseases, skin diseases, burn wounds, smoke inhalation, intoxication, severe blood loss, food poisoning, chemotherapy, radiation therapy, severe trauma, liver diseases and other immune deficiency/compromised conditions Considering the unexpected, and surprising, immune modulating activity of ectophosphates, the present invention, according to another aspect, relates to the use of an ectophosphatase for the preparation of a medicament for increasing the activity of the immune system of a mammal, preferably a human mammal, wherein, preferably, the ectophosphatase is selected from the group consisting of alkaline phosphatase, nucleotidase (CD73) and apyrase (CD39).

According to yet another aspect, the present invention relates to a method for increasing the activity of the immune system of a mammal, preferably a human mammal, comprising administering to said mammal a therapeutically effective amount of an ectophosphatase, wherein, preferably, the ectophosphatase is selected from the group consisting of alkaline phosphatase, nucleotidase (CD73) and apyrase (CD39).

According to still another aspect, the present invention relates to a pharmaceutical composition comprising an ectophosphatase and one or more pharmaceutically acceptable carriers and/or diluents, wherein, preferably, the ectophosphatase is selected from the group consisting of alkaline phosphatase, nucleotidase and apyrase.

BRIEF DESCRIPTION OF THE DRAWINGS

Below, the present invention will be further detailed in the following examples wherein reference is made to the accompanying figures wherein.

DETAILED DESCRIPTION OF THE INVENTION

EXAMPLES

Example 1

A bolus of AP (bIAP), followed by a 36 hours intravenous infusion (5.6 IU/kg/hour) was intravenously administered to patients resulting in a peak plasma level of AP immediately after administration with a kinetic profile compatible with the administered AP. (bIAP, t1/2 about 10 minutes).

Figure 1:
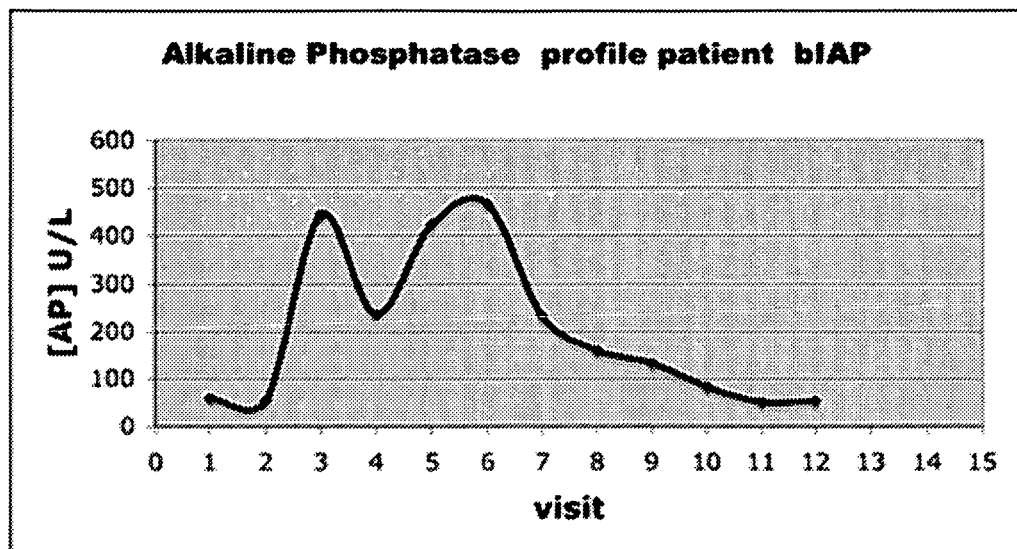
FIG. 1: shows the alkaline phosphatase (AP) kinetics in a representative CABG patient receiving bovine Intestinal AP for 36 hours (Bolus prior to surgery), followed by infusion with 5.6 units kilo bodyweight for period of 36 hours). A second peak of plasma AP activity surfaces between 1.5 and 12 hours post-surgery is observed with prolonged plasma residence time. Alkaline phosphatase (AP) kinetics in a representative placebo patient is shown for comparison.
Figure 1:
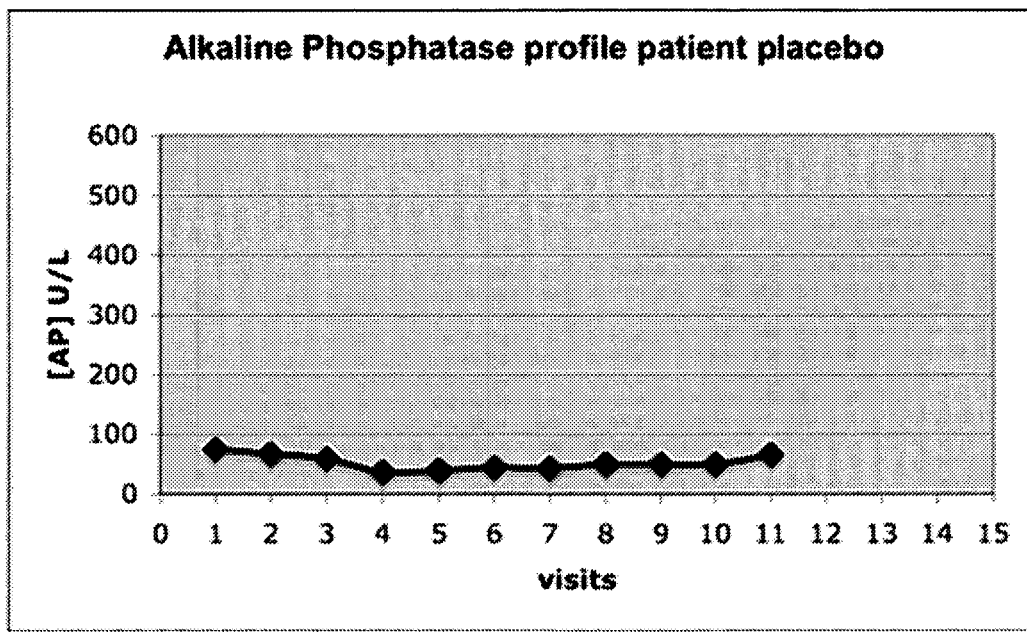
Figure 3:
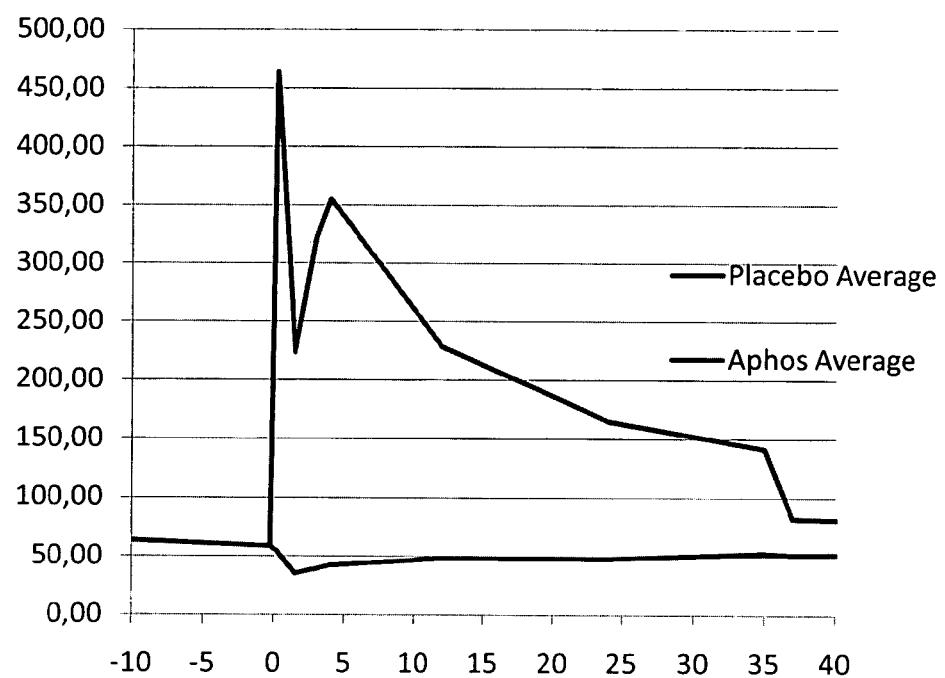
FIG. 3: Average alkaline phosphates levels as compared to placebo in all patients tested. It is noted that in placebo patients levels of circulating aphos fall sharply from base levels with about 50%.

Referring to FIGS. 1 and 3, it is shown that after an initial bolus with bovine intestinal alkaline phosphatase (bIAP), the total plasma level of alkaline phosphatase increases and, subsequently, is cleared fast. However a second peak is observed between 1.5 and 35 hours, peaking at 4-12 hours post surgery.

This second peak of alkaline phosphatase observed in bIAP treated patients is not the result of the continued bIAP infusion during 36 hours since the amount of infused APhos would only account for an increase of normal base plasma levels. The plasma residence time of this alkaline phosphatase is prolonged up to about T1/2 of about 22 hours, compatible with endogenous tissue non specific alkaline phosphatase.

In placebo treated patients, no rise in Alkaline phosphatase plasma levels is observed but rather a sharp decrease in plasma levels 1.5 hours after onset of surgery. Next, a slow return (increase) to normal staring levels is observed over the subsequent hours (followed during 35 hours).

It is evident that plasma levels of endogenous Alkaline Phosphatase fall sharply upon surgery and are restored in due time. Therefore it can be stated that endogenous plasma alkaline phosphatase is "used" during surgery and is not replenished in a fast manner.

Figure 2:
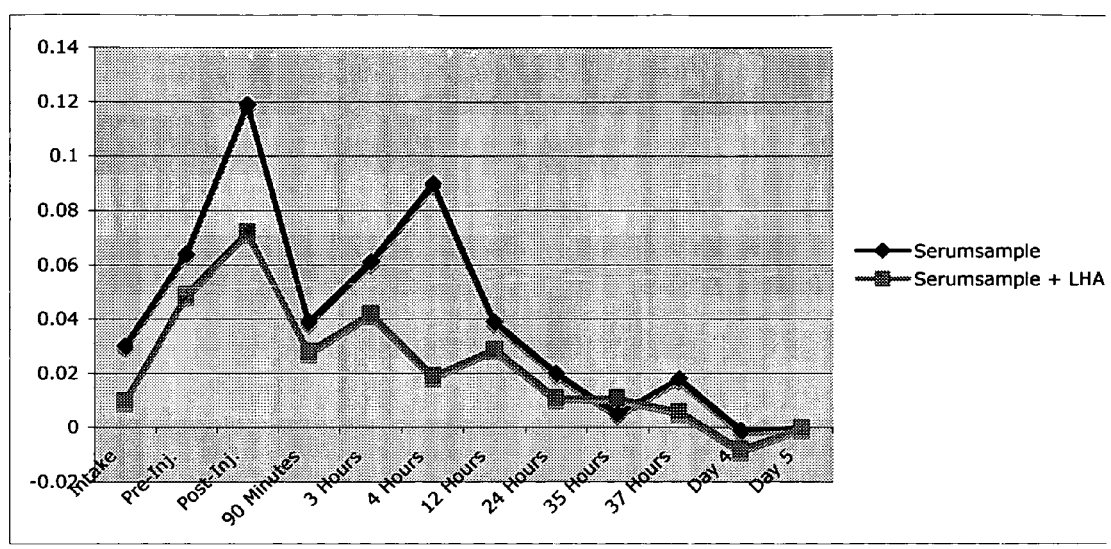
FIG. 2: shows that the induced endogenous alkaline phosphatase (AP) is a tissue Non Specific Type as evidenced by L-HA sensitivity of second peak. Induction of endogenous AP (peak at t=4 hours post start of surgery) after supplemental AP administration prior to surgery. Effects of 5 mM L-HA on measured AP in blood plasma of a CABG patient treated with administered supplemental bIAP

Surprisingly it was found that by using supplemental AP as prophylactic treatment in patients undergoing surgery an induction is evoked of an endogenous secondary AP (FIGS. 1 and 3) that is inhibited by L-HA (L-homo arginin), known to act as an inhibitor of tissue non specific AP (FIG. 2)

The endogenous AP that emerges is an AP with the kinetic profile having an overall apparent plasma residence time in the order of about 20-22 hours. This induced type phosphatase was sensitive for 1-homoarginin and consequently is most likely Tissue Non Specific AP (e.g. liver type).

Example 2

The above results demonstrate the suitable of prophylactic treatment with ectophosphatases in Surgery induced ischemia-reperfusion damage, trauma, radiotherapy, chemotherapy, acute travelers disease, health worker protection, acute protection, and boosting innate immune functionality in, for example, immunocompromised patients.

Boosting Endogenous AP in Order to Combat Pro-Inflammatory Down Stream Effects of Local or Distant Ischemia-Reperfusion Damage by Parenteral Administration of a Suitable Formulation of AP.

The phosphatase may be administered intravenous, subcutaneous, intraperitoneal, by inhalation or oral. The latter will be opportune in case of a formulation with high bioavailability. Since the boost reaction of endogenous phosphatase shows kinetics that suggest de-novo synthesis or delayed release from unknown depots, also "slow-release" formulations will be applicable that release their content in a period of up to 6 hours, thereby establishing a circulating phosphatase concentration level that may act as trigger for endogenous phosphatase booster response.

Upon surgery, endogenous alkaline phosphatase plasma levels fall sharply only to be restored and returned to normal levels over a time period far exceeding surgery time. From this, supplementation of lost alkaline phosphatase prior to or even during surgery will compensate and protect the patients from an ischemia-reperfusion derived "stranger (e.g endotoxin) or danger (e.g. extracellular nucleotides) signal" pro-inflammatory insult.

Supplemental Circulating Levels or Exposed Physiological Active AP are Important in Conditions where not Sufficient Endotoxin-Binding Capacity is Available.

Supplementation of AP to patients with e.g liver disease may help to combat resulting SIRS or endotoxemia. In Chronic Liver Disease (CLD) the total AP activity in plasma is increased with progression of pathology. Thus increasing amounts of total AP (APhos, ALP) are observed chronic hepatitis (CH), liver cirrhosis (LC) and hepatocellular carcinoma (HCC). The source of this increased AP is different. Thus a predominant increase of High molecular weight Intestinal AP (HIALP) is observed in LC (increase from 21.1% to 49.3 of total), where this intestinal AP showed less increase in HCC.

HIALP is intestinal phosphatase that is GPI anchored and is secreted (shed) in plasma and binds to various substances. In this regard HIALP much reflects the polymeric state of AP (ALP5). Also in primary biliary cirrhosis and autoimmune hepatitis the amount of HIALP is about 44.4% of total.

The increase of intestinal derived HIALP is a consequence of reduced TNSAP in plasma, due to liver malfunctioning. Diabetes mellitus, liver cirrhosis, and chronic renal failure all show high frequency of variant intestinal ALP up to 45% (from control 23.8%). This variant intestinal ALP has a membrane-binding domain.

LPS, to a certain extend is bound and neutralised in plasma. It was reported that patients with alcoholic liver disease show reduced endotoxin-binding capacity and correlated severity of disease with the capacity to cope with translocating intestine-derived endotoxin entering circulation. Factors that can bind and neutralize endotoxins in blood are amongst others high and low density lipoproteins and bactericidal/permeability-increasing protein (BPI) and anti-endotoxin antibodies.

Prophylaxis: Application in Travellers/Health Workers Protection Against Gut, Respiratory and Skin Inflammation.

Administration of phosphatase upon initiation of physical labour activities (i.e. health authority workers) in environments that are highly contagious may enable additional protection that suffices for a limited time. Since the activity of phosphatase that is administered parenteral is immediate, also travellers may be given a parenteral dose in case of acute infection-mediated inflammation.

Such dosing may be given subcutaneous, intramuscular or intraperitoneal. Albeit that infection as such will not prevented, the detrimental systemic inflammatory responses to such infections will be combated more efficacious (phosphatase does not act as an antimicrobial moiety, but acts on preventing down stream pro-inflammatory effects). Therefore, boosting endogenous ectophosphatase with relatively stable plasma residence time of 20-22 hours will protect against pathogen-induced inflammation. Next to prophylaxis with appropriate vaccines, antibiotics, antivirals or anti-fungal compounds thus improved protection can be ascertained.

Parenteral Application of (Alkaline) Phosphatase After Severe Trauma.

Traumatic conditions like originating from severe burn wounds, smoke inhalation/intoxication or severe blood loss or massive food poisoning is a direct cause to SIRS induction. By administrating phosphatase one prevents the detrimental pro-inflammatory down stream effects of such traumatic condition by boosting the physiological active endogenous phosphatase pool, which subsequently can actto prevent further generation of proinflammatory moieties.

Prophylactic Supplementation of AP Prior to Radiation or Chemotherapeutic Treatment, in Order to Boost Innate Immune Functionality.

Radiation and chemotherapeutic treatment are correlated to massive destruction of cellular systems, leading to pro-inflammation. Also resistance against infection and subsequent inflammation is reduced. AP supplementation prior to treatment will boost the endogenous resistance to treatment-mediated inflammation and thus will ameliorate the condition and quality of life of the affected patient.

Example 3

Alkaline phosphatase is an ubiquitous endogenous ecto-enzyme enzyme in the human body. This ectophosphatase is widely expressed in many organs that are exposed directly or indirectly to the external environment, like the gastrointestinal tract and the lungs.

A physiological role for alkaline phosphatase was proposed in 1997 by Poelstra et al (1). Alkaline phosphates dephosphorylates and thereby detoxifies endotoxins (lipopolysaccharides) at physiological pH levels (2; 3). Extracellular nucleotides are also substrates for alkaline phosphatase. These nucleotides, normally retained in the cytosol, are released into the extacellular space when the cells are damaged cells and are sensed as 'danger' signals to the innate immune system. Ectophosphatases convert these nucleotides into non-inflammatory nucleosines (4). Hypoxic conditions, resulting from surgical trauma may result in ischemia and subsequent inflammatory reactions.

During cardiopulmonary bypass (CPB) hypoperfusion of the gut may result in a loss of barrier function, and as a consequence bacterial endotoxins, normally confined to the lumen of the intestine by a barrier of endovascular cells, may enter the systemic circulation (5-7). The amount of endotoxin release is seems to be related to cross clamp time and CPB time (7). Endotoxin release has been recognised as an important factor in the inflammatory response following CPB.

Previous animal studies with the use of intravenous alkaline phosphatase showed promising therapeutics effects in reducing the inflammatory response (8-10).

In a clinical study in severe sepsis patients continuous infusion of bIAP significantly improves their renal function (11). Tuin et al. (12) demonstrated that, after LPS administration, in rat liver both in vitro and in vivo, de-novo synthesis of alkaline phosphatase occurs.

Materials and Methods

In the present double blind, placebo-controlled study, patients undergoing elective non-emergent coronary artery bypass grafting were randomized to receive either bovine intestinal alkaline phosphatase (bIAP) or matching placebo. The study was approved by the Institutional Review Board on the 16th of March 2006. The study drug bIAP was manufactured by Biozyme ltd (Bleanavon, Wales, UK) and Alloksys Life Sciences B.V. (Bunnik, The Netherlands). The placebo consisted of a sterile infusion solution for infusion containing no bIAP (content 1 ml) in a 2 ml vial in 1 mL of an aqueous buffer containing 20 mM Tris-HCl, 5 mM Magnesium Chloride, 0.1 mM Zinc Chloride, pH 7.3, with 25% glycerol and human serum albumin as stabilizer.

Alkaline Phosphatase Measurement

Alkaline phosphatase was measured using a PNPP (p-nitrophenol phosphate) kinetic assay (13). Samples were defrosted and warmed gradually to 21 degrees Celsius. Two hundred (200) µL of a serum sample was mixed with 1 mL of PNPP-substrate (Sigma-Aldrich Chemie BV, Zwijndrecht, The Netherlands) and $MgCl_2$ (final concentration 2 mM) in a Tris-glycerin buffer at pH 9.6 10 mm cuvette. Samples were measured kinetically at 405 nm on Biorad Smartspec photospectrophotometer for 60 seconds in with intervals of 20 seconds. Bone alkaline phosphatase activity was measured by an immunocapture assay from METRA Biosystems.

Enzyme Inhibition

L-homoarginine (LHA) (Sigma-Aldrich Chemie BV, Zwijndrecht, The Netherlands) was used as a tissue non-specific alkaline phosphatase (TNSALP) inhibitor, to investigate the origin of the alkaline phosphatase. LHA has minimal influence on bIAP, but does have impact on inhibits tissue non-specific alkaline phosphatase ('LBK') activity (14).

For the inhibition assay, bIAP was diluted to a concentration of 0.08 U/L and 100 µL of sample was added to to a glass tube. Five mM LHA (final concentration) was added and this was gently mixed and incubated at room temperature for 5 minutes. Next a PNPP Kinetic assay was carried out similarly as described above but now measurements were taken for 180 seconds with in intervals of 20 seconds. For pharmacokinetic purposes, human alkaline phosphatase levels were measured at the Catharina Hospital Laboratory by routine clinical chemistry methods. (Cobas-Bio centrifugal analyser, Roche Diagnostics, Switzerland).

Study Drug Administration, Rationale for Safety and Randomization

The study drug bovine Intestinal Alkaline Phosphatase (bIAP) or matching placebo was administered as an intravenous bolus of 1000 International Units (IU), just prior to induction of anaesthesia, directly followed by intravenous continuous infusion of 5.6 U/kg units per kilogram bodyweight per hour at a flow rate of 4 mL/h for 36 hours in order to maintain supranormal levels of alkaline phosphatase in blood. A phase I bIAP study demonstrated that 72-hour continuous infusions of up to a total of 48.000 IU (at 80 kg bodyweight) of bIAP was safe and well tolerated.

Over a period of 90 days after administration, no immune incompatibility was found as evidenced by lack of induction of specific antibodies to bIAP. No drug-related adverse events were observed (15). The responsible trial pharmacist at the pharmacy department performed randomization of the study drugs.

CPB Technique

After median sternotomy and preparation of the internal mammary artery, all patients received 3 mg/kg heparin (Leo Pharma, the Netherlands) intravenously. Because a low dose (200 ml, 1000 KIU/mL) Aprotinin (Bayer Health Care Pharmaceuticals) was added to the prime in all patients, heparin administration of 1 mg/kg was repeated every hour during CPB, regardless of the ACT.

The CPB circuit consisted of a Biomedicus BP80 centrifugal pump (Medtronic, Minneapolis, Minn., USA), a membrane oxygenator (Sorin Srl. Avant, Mirandola, Italy or Medtronic Affinity, Minneapolis, Minn., USA, or Gish Biomedical, Rancho Santa Margaria, Calif., USA), a custom made collapsible venous reservoir (Sorin Biomedica, Mirandola, Italy) and a D980 Avant dual chambered hard-shell venous cardiotomy reservoir (Sorin Srl., Mirandola, Italy). The priming fluid consisted of 800 mL NaCl 0,9%, 500 mL Voluven® (Fresenius Kabi, the Netherlands), 200 mL Mannitol 20% (Baxter Health Care, the Netherlands), 200 mL Aprotinin 1000 KIU/mL, 25 ml NaHCO3 8,4% and heparin 7500 IU. Normothermic cardiopulmonary bypass was applied in all patients. For myocardial protection, either warm blood cardioplegia or st. Thomas cold cristalloid cardioplegia was used, depending on the surgeon's preference. At the end of cardiopulmonary bypass heparin was neutralized with Protamine chloride (Valeant Pharmaceuticals, the Netherlands).

Statistical Analysis

Evaluation was performed with help of the SAS System (Software Release 9.13). Data were checked for completeness and a second plausibility check was performed. The Wilcoxon signed rank test was used to compare continuous variables of two groups, the Pearson's chi-square test was used to investigate the frequency (percentage) to of Parameters; and a probability of $p<0.05$ was considered to be statistically significant. However, apart from the primary endpoint (frequency of major pro-inflammatory reaction) all p-values given are descriptive only.

Results

A total of 63 patients (bIAP n=32, placebo n=31) were was enrolled in this study. No significant safety concerns were identified. Except for BMI which was significantly higher in the placebo group (25.7±2.7 versus 27.4±3.5, p=0.037), there were no statistically significant differences in demographic data. The two groups were similar with regard to the number of grafts, CPB- and cross clamp time and type of cardioplegia used. Furthermore, there were no statistically significant differences in postoperative outcome.

As described elsewhere (ref Kats et al, 2008), a fulminant inflammatory response was only observed in a small group of patients in the placebo group. These 5 patients showed a fulminant TNFα response (mean peak level 108 pg/mLl, range 0.10-476 pg/mL) observed at 4 hours post induction of surgery. This TNFα response was followed by an increase in plasma levels of IL-6 (mean peak level 683 pg/mL, range 9-2386 pg/mL) and IL-8 (mean peak level 642 pg/mL, range 13-1696 pg/mL). Such a post-surgical TNFα response was not observed in the bIAP group (p<0.02). The overall inflammatory response as deduced from cytokine levels, C reactive protein (CRP), AST and ALT was low both in the bIAP and the placebo group.

Postsurgical Plasma Alkaline Phosphatase Levels

Preoperative levels of alkaline phosphatase were 70.03±17.12 IU/L in the bIAP treated group, and 70.50±15.63 IU/L in the placebo treated group (p=ns). In the placebo treated group in 31 out of 31 patients we found a reduction of plasma alkaline phosphatase levels within 2 hours post surgery (34.89±9.59 IU/L). This reduction in plasma alkaline phosphatase levels was followed by normalisation of this level after 24 hours.

In the bIAP treated group in all of the 32 patients we found an initial rise of plasma alkaline phosphatase levels due to bolus administration (464±176 IU/L). Next to the initial rise a significant increase of plasma alkaline phosphatase at about 4-6 hours post-surgery was observed (355±95 IU/L). This alkaline phosphatase could be inhibited by L-homoarginine and thus likely represents Tissue Non Specific Alkaline Phosphatase (TNSALP-type alkaline phosphatase) (14). Through isoenzyme analysis it was excluded that this postsurgical rise of plasma alkaline phosphatase could be attributed to rise of bone type alkaline phosphatase. Hence the most likely source is liver type alkaline phosphatase.

Interestingly, the reduction of postsurgical alkaline phosphatase in placebo treated patients also affects the amount of circulating bone type alkaline phosphatase with similar percentages as total alkaline phosphatase, although bone type alkaline phosphatase—as stated above—is not induced in parallel with the apparent postsurgical plasma TNSALP-type alkaline phosphatase.

Discussion

The alkaline phosphatase family consists of tissue non-specific alkaline phosphatases, like liver-, bone- and kidney alkaline phosphatase, and tissue specific alkaline phosphatase, like intestinal-, placenta- and placenta-like alkaline phosphatase (16).

A physiological role for alkaline phosphatase has been proposed by Poelstra et al. in 1997 (1). Intestinal alkaline phosphatase is able to detoxify endotoxin, a product of gram-negative bacteria, which is abundantly present in the external environment and in the intestinal lumen tract. The phosphorylated lipid-A moiety of the endotoxin, considered to be essential for its biological actions, is a substrate for alkaline phosphatase, which enzymatically dephosphorylates the toxic lipid-A part into monophosphoryl lipid-A, a non-inflammatory metabolite, and inorganic phosphate (2; 3).

Next to LPS as substrate for alkaline phosphatase, this ectophosphatase also converts pro-inflammatory nucleotides that are released during ischemic insults and which normally lead to a local rise in pro-inflammatory cytokines like TNFα at the surgical site. Torre Amione demonstrated that local TNFα rise during cardiac surgery could be prevented by administration of a TNFα blocker like Etanercept (17). Similarly to this finding the present study shows that bIAP is capable of preventing a fulminant TNFα response, since such a TNFα response was observed in the placebo group only.

During CABG with the use of CPB increased LPS translocation from the intestine occurs (18; 19), Moreover it has been demonstrated that at the site of surgery, depending on CPB time and cross clamp, time ischemic insults occur followed by a local rise in nucleotides. Both ischemia-reperfusion mediated endotoxin and extra-cellular released nucleotides are potent-inflammatory triggers and are a substrate for both supplemental and endogenous alkaline phosphatase.

Normally LPS travels with chyme and it is taken up by Kupffer cells and hepatocytes. This LPS is proposed to be predominantly detoxified through the activity of intestinal type alkaline phosphatase and plasma resident alkaline phosphatase. Several authors reported that Kupffer cells may function to clear the alkaline phosphatase-LPS conjugates from the circulation, thereby reducing the total alkaline phosphatase levels (2; 20), which is also demonstrated in our study in the placebo group, where there is a initial reduction of plasma alkaline phosphatase.

In the absence of a sufficient amount of alkaline phosphatase activity, its endotoxin clearance function may be suboptimal, resulting in further aggravation of endotoxin-mediated inflammatory effects. Therefore, we supplemented bovine alkaline phosphatase in our study to combat endotoxin-induced inflammation in CABG with the use of CPB.

An interesting finding in this study is the difference in alkaline phosphatase levels between the bIAP and the placebo treated group. In placebo treated patients a reduction of plasma alkaline phosphatase levels was measured 2 hours post surgery. Normalised plasma levels were observed after 24 hours. Reduction of plasma alkaline phosphatase after endotoxin administration levels was reported previously by Verweij et al. in animal studies (20).

In the bIAP treated group, an initial rise in alkaline phosphatase plasma level due to the bolus administration was observed. The kinetic behaviour of this plasma alkaline phosphatase 1 was compatible with the administered alkaline phosphatase, with a physical half-life of about 10 minutes (8).

Next to the initial increase in alkaline phosphatase level, a significant secondary increase of plasma alkaline phosphatase at about 4-6 hours post-surgery was observed. This endogenous alkaline phosphatase is inhibited by L-homoarginine and thus likely represents tissue non-specific alkaline phosphatase, with a physical half life of about 20 hours (14). As judged from the post-surgical amount of this tissue non-specific alkaline phosphatase circulating, the most likely source is liver type alkaline phosphatase, since it was demonstrated that the other abundant source in plasma, being bone type alkaline phosphatase was not increased.

The present study shows that alkaline phosphatase prophylaxe improves the defence against a new inflammatory insult by triggering the release of sustainable alkaline phosphatase in the circulation.

The surprising implication of this finding has significant consequences. Alkaline phosphatase may act like an acute phase protein, high levels of physiological active alkaline phosphatase having a protective anti-inflammatory effect. The pre-operative plasma levels may predict clinical outcome in acute inflammation in a manner similar to the that reported for high plasma anti-endotoxin antibody levels (21; 22).

Accordingly, patients are protected by pre-treatment with physiological active alkaline phosphatase which will increase their endogenous physiological levels.

Conclusion

Intravenous bolus administration of alkaline phosphatase in patients undergoing coronary artery bypass grafting results in a subsequent rise in circulating plasma alkaline phosphatase levels 4 to 6 hours after the start of surgery. The origin of this alkaline phosphatase is attributed to tissue non-specific alkaline phosphatase, most likely liver-type alkaline phosphatase. This endogenous alkaline phosphatase may play a role in the innate immune defence system.

References (1) Poelstra K, Bakker W W, Klok P A, Hardonk M J, Meijer D K. A physiologic function for alkaline phosphatase: endotoxin detoxification. Lab Invest 1997 March; 76(3):319-27.

(2) Bentala H, Verweij W R, Huizinga-van der Vlag A, van Loenen-Weemaes A M, Meijer D K, Poelstra K. Removal of phosphate from lipid A as a strategy to detoxify lipopolysaccharide. Shock 2002 Dec.; 18(6):561-6.

(3) Poelstra K, Bakker W W, Klok P A, Kamps J A, Hardonk M J, Meijer D K. Dephosphorylation of endotoxin by alkaline phosphatase in vivo. Am J Pathol 1997 October; 151(4):1163-9.

(4) Eckle T, Fullbier L, Wehrmann M, Khoury J, Mittelbronn M, Ibla J, et al. Identification of ectonucleotidases CD39 and CD73 in innate protection during acute lung injury. J Immunol 2007 Jun. 15; 178(12):8127-37.

(5) Oudemans-van Straaten H M, Jansen P G, Hoek F J, van Deventer S J, Sturk A, Stoutenbeek C P, et al. Intestinal permeability, circulating endotoxin, and postoperative systemic responses in cardiac surgery patients. J Cardiothorac Vasc Anesth 1996 Feb.; 10(2):187-94.

(6) Nilsson L, Kulander L, Nystrom S O, Eriksson O. Endotoxins in cardiopulmonary bypass. J Thorac Cardiovasc Surg 1990 November; 100(5):777-80.

(7) Rocke D A, Gaffin S L, Wells M T, Koen Y, Brock-Utine J G. Endotoxemia associated with cardiopulmonary bypass. J Thorac Cardiovasc Surg 1987 June; 93(6):832-7.

(8) Beumer C, Wulferink M, Raaben W, Fiechter D, Brands R, Seinen W. Calf intestinal alkaline phosphatase, a novel therapeutic drug for lipopolysaccharide (LPS)-mediated diseases, attenuates LPS toxicity in mice and piglets. J Pharmacol Exp Ther 2003 November; 307(2):737-44.

(9) van Veen S Q, Dinant S, van Vliet A K, van Gulik T M. Alkaline phosphatase reduces hepatic and pulmonary injury in liver ischaemia—reperfusion combined with partial resection. Br J Surg 2006 April; 93(4):448-56.

(10) van Veen S Q, van Vliet A K, Wulferink M, Brands R, Boermeester M A, van Gulik T M. Bovine intestinal alkaline phosphatase attenuates the inflammatory response in secondary peritonitis in mice. Infect Immun 2005 July; 73(7):4309-14.

(11) Pickkers P, Snellen F, Rogiers P, Bakker J, Jorens P, Meulenbelt J, et al. Clinical pharmacology of exogenously administered alkaline phosphatase. Eur J Clin Pharmacol 2008 Dec. 2.

(12) Tuin A, Huizinga-van d, V, van Loenen-Weemaes A M, Meijer D K, Poelstra K. On the role and fate of LPS-dephosphorylating activity in the rat liver. Am J Physiol Gastrointest Liver Physiol 2006 February; 290(2):G377-G385.

(13) Bergmeyer H. U. Methods of Enzymatic Analysis. II [3rd edition], 269-270. 1983.

(14) Lin C W, Fishman W H. L-Homoarginine. An organ-specific, uncompetitive inhibitor of human liver and bone alkaline phosphohydrolases. J Biol Chem 1972 May 25; 247(10):3082-7.

(15) Ramael S. A phase I study to investigate the safety, tolerability, pharmacokinetics and pharmacodynamics of Calf Intestinal Alkaline Phosphatase 72-h infusions in healthy volunteers. SGS Biopharma Research Unit Stuivenberg, SGS Biopharma B103613 report, 2004. 2008.

(16) Harris H. The human alkaline phosphatases: what we know and what we don't know. Clin Chim Acta 1990 Jan. 15; 186(2):133-50.

(17) Torre-Amione G, Wallace C K, Young J B, Koerner M M, Thohan V, McRee S, et al. The effect of etanercept on cardiac transplant recipients: a study of TNFalpha antagonism and cardiac allograft hypertrophy. Transplantation 2007 Aug. 27; 84(4):480-3.

(18) Andersen L W, Baek L, Degn H, Lehd J, Krasnik M, Rasmussen J P. Presence of circulating endotoxins during cardiac operations. J Thorac Cardiovasc Surg 1987 January; 93(1):115-9.

(19) Kharazmi A, Andersen L W, Baek L, Valerius N H, Laub M, Rasmussen J P. Endotoxemia and enhanced generation of oxygen radicals by neutrophils from patients undergoing cardiopulmonary bypass. J Thorac Cardiovasc Surg 1989 September; 98(3):381-5.

(20) Verweij W R, Bentala H, Huizinga-van d, V, Miek vL-W, Kooi K, Meijer D K, et al. Protection against an *Escherichia coli*-induced sepsis by alkaline phosphatase in mice. Shock 2004 August; 22(2):174-9.

(21) Bennett-Guerrero E, Ayuso L, Hamilton-Davies C, White W D, Barclay G R, Smith P K, et al. Relationship of preoperative antiendotoxin core antibodies and adverse outcomes following cardiac surgery. JAMA 1997 Feb. 26; 277(8):646-50.

(22) Rothenburger M, Soeparwata R, Deng M C, Schmid C, Berendes E, Tjan T D, et al. Prediction of clinical outcome after cardiac surgery: the role of cytokines, endotoxin, and anti-endotoxin core antibodies. Shock 2001; 16 Suppl 1:44-50.

(23) Mangano D T, Miao Y, Vuylsteke A, Tudor I C, Juneja R, Filipescu D, et al. Mortality associated with aprotinin during 5 years following coronary artery bypass graft surgery. JAMA 2007 Feb. 7; 297(5):471-9.

The invention claimed is:

1. A prophylactic method for reducing the risk of developing an inflammatory disease comprising intravenously administering an ectophosphatase to a mammal, wherein said ectophosphatase is administered in an amount effective to result in induction of endogenous ectophosphatase levels.

2. The method according to claim 1, wherein said ectophosphatase is selected from the group consisting of alkaline phosphatase, nucleotidases, and apyrases.

3. The method according to claim 2, wherein the ectophosphatase is selected from the group consisting of CD39, CD73, and ATP-ADPase.

4. The method according to claim 1, wherein said method further comprises preventing an increase in levels of inflammatory markers in the mammal.

5. The method according to claim 1, wherein said risk of developing said inflammatory disease results from a condition in which inflammatory markers are increased.

6. The method according to claim 5, wherein said condition is selected from the group consisting of surgery, digestive tract diseases, respiratory diseases, skin diseases, burn wounds, smoke inhalation, intoxication, severe blood loss, food poisoning, chemotherapy, radiation therapy, severe trauma liver diseases, and immuno compromised conditions.

7. The method according to claim 1, wherein said mammal is a human mammal.

8. The method of claim 1, wherein the induction of endogenous ectophosphatase levels is provided by administration of a bolus of exogenous ectophosphatase followed by supplemental continuous administration of ectophosphatase.

\* \* \* \* \*